United States Patent [19]

Kuwazima et al.

[11] 4,419,439
[45] Dec. 6, 1983

[54] PROCESS FOR FORMING PHOTOGRAPHIC IMAGES

[75] Inventors: Shigeru Kuwazima; Eiichi Kato; Minoru Yamada, all of Minami-ashigara, Japan

[73] Assignee: Fuji Photo Film Co., Ltd., Kanagawa, Japan

[21] Appl. No.: 322,053

[22] Filed: Nov. 16, 1981

[30] Foreign Application Priority Data

Nov. 14, 1980 [JP] Japan ............................ 55-160325

[51] Int. Cl.³ .............................................. G03C 7/00
[52] U.S. Cl. .................................... 430/375; 430/566; 430/542; 430/376; 430/377; 430/380; 430/552; 430/543; 430/546; 430/382
[58] Field of Search ............... 430/375, 566, 542, 376, 430/377, 380, 552, 546, 543, 382

[56] References Cited

U.S. PATENT DOCUMENTS 2,322,027  6/1943  Jelley et al. ...................... 430/546
3,146,104  8/1964  Yackel et al. ..................... 430/566
3,723,119  3/1973  Yoshida et al. .................... 430/302

Primary Examiner—Won H. Louie, Jr.
Attorney, Agent, or Firm—Sughrue, Mion, Zinn, Macpeak and Seas

[57] ABSTRACT

A process for forming a photographic image comprising imagewise exposing a silver halide photographic light-sensitive material to light and processing the silver halide photographic light-sensitive material with an alkaline processing solution, wherein the improvement comprises the silver halide photographic light-sensitive material contains a compound represented by formula (I)

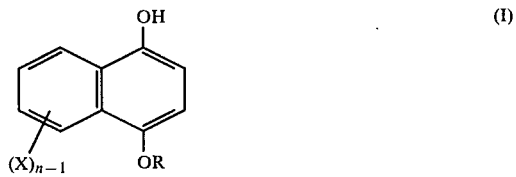

wherein R represents an alkyl group having from 6 to 22 carbon atoms, a substituted alkyl group having from 6 to 22 carbon atoms, an aryl group having from 6 to 22 carbon atoms, a substituted aryl group having from 6 to 22 carbon atoms, an alkenyl group having from 6 to 22 carbon atoms, a substituted alkenyl group having from 6 to 22 carbon atoms or an aralkyl group having from 7 to 22 carbon atoms; X represents an alkyl group having from 1 to 4 carbon atoms, an alkoxy group having from 1 to 6 carbon atoms, or a halogen atom; and n represents an integer from 1 to 3.

According to the process, a high maximum image density is obtained using a silver halide photographic light-sensitive material containing a low amount of coated silver.

24 Claims, No Drawings

PROCESS FOR FORMING PHOTOGRAPHIC IMAGES

FIELD OF THE INVENTION

The present invention relates to a novel process for forming photographic images, and, more particularly, to a process for obtaining suitable image density from a silver halide photographic light-sensitive material that contains a relatively low amount of coated silver.

BACKGROUND OF THE INVENTION

In ordinary processes for forming black-and white photographic images, a latent image is formed in a silver halide photographic light-sensitive material through imagewise exposure, and the light-sensitive material is then developed with a developing solution containing a common black-and-white developing agent such as hydroquinone, metol, phenidone, etc. The metallic silver formed in the latent image areas is useful as a black-and-white image. Upon development processing, the oxidation product of the developing agent formed is removed from the system as an unnecessary material.

Imagewise formation of a dye utilizing the oxidation product of the developing agent provides an image density which is the sum of the silver density and the dye density, and, as a result, a higher image density can be obtained using a specific amount of coated silver.

Various processes have been proposed directed to reducing the amount of silver. For example, there is a process for forming a silver image and a dye image at the same time using a coupler developer compound having in the molecule a residue which functions as a developing agent and a residue which functions as a coupler capable of coupling with an oxidation product of the former residue to form a dye, thus reducing the amount of coated silver, as described in U.S. Pat. Nos. 3,615,509 and 3,622,629. Also, there is a process for forming a black image using both p-phenylenediamine derivative and phenol or naphthol, or an active methylene compound, as described in U.S. Pat. No. 2,181,944. Furthermore, a black image has been formed using, as a developing agent, 3-aminopyrazolobenzimidazole, and, as a coupler, an active methylene compound as described in West German Pat. No. 1,158,836.

British Pat. No. 492,518 and West German Pat. No. 537,923 disclose a process for forming a black image by mixing couplers commonly used in the currently employed color photographic process which can form yellow, magenta, and cyan dyes, respectively, and conducting color development. Japanese Patent Application (OPI) No. 37539/72 (the term "OPI" as used herein refers to a "published unexamined Japanese patent application") discloses a process for forming a dye image and a silver image at the same time by conducting color development in the presence of a color coupler and fixing without removing silver, thus reducing the amount of silver required to be coated. Japanese Patent Application (OPI) No. 42725/77 discloses a process for forming a black image by using an m-aminophenol derivative as a coupler, Japanese Patent Application (OPI) No. 57827/77 discloses a process for obtaining a black image by using a polyfunctional coupler and a polyfunctional developing agent, U.S. Pat. No. 4,126,461 discloses a process for obtaining a black image by using a diffusion resistant resorcinol derivative as a coupler, and Japanese Patent Application (OPI) No. 123032/79 discloses a process for obtaining a black image by using a dihydroxy naphthalene derivative.

However, the foregoing processes have not been capable of being put into satisfactory practical use, since they have several disadvantages, such as (1) that it is difficult to obtain a high image density for the amount of coated silver, (2) that the materials for forming the images are comparatively expensive, (3) that the fastness of the image formed is insufficient, (4) that skin lesions (i.e., poisoning) may occur upon exposure to color developing agent, particularly p-phenylenediamine derivatives, and the like.

Furthermore, in British Pat. No. 1,122,085, a process for forming images comprising a silver image and a dye image by developing with a processing solution containing both a water-soluble 4-alkoxy-1-naphthol derivative and a 1-phenyl-3-pyrazolidinone derivative is disclosed, and it is also described that the combination of a 1-phenyl-3-pyrazolidinone derivative and an alkoxynaphthol has a high development activity and provides high efficiency in the development of silver and the formation of dye, resulting in obtaining a high optical density. However, as illustrated in Examples hereinafter, the alkoxynaphthols described therein are very rapidly oxidized by air in the presence of an alkali to form compounds which are slightly soluble in water, or they form dyes which are insoluble in a processing solution due to self-coupling. When a photographic light-sensitive material is processed in a developer solution containing alkoxynaphthols which are readily oxidized by air as described above, severe fog is formed, or the dyes formed adhere to the light-sensitive material, which are troublesome in practical use.

By incorporating the alkoxynaphthols described above into a photographic light-sensitive material, such degradation of the developer solution due to the oxidation of alkoxynaphthols by air can be prevented only when a fresh developer solution is employed. However, as illustrated in Examples hereinafter, when the alkoxynaphthols described above are used, the compounds dissolve out little by little from the light-sensitive materials and accumulate in the processing solution when the processing solution is repeatedly used. As a result, oxidation by air occurs in the same manner as in the case when the compound is originally added to the developer solution. Thus, the basic problem still occurs even if the alkoxynaphthols are incorporated in the photographic material.

SUMMARY OF THE INVENTION

An object of the present invention is to provide a process for forming an image which is capable of obtaining a high maximum density using a silver halide photographic light-sensitive material containing a relatively low amount of coated silver.

Another object of the present invention is to provide a process for forming an image safely, free from the possibility of poisoning by a color developing agent.

Still another object of the present invention is to provide a process for forming an image using a developer solution which is excellent in durability and running stability.

Still another object of the present invention is to provide a process for forming an image having substantially black or blue-black color.

Other objects of the present invention will become apparent from the following detailed description and examples.

These objects of the invention have been attained by forming a photographic image comprising a silver image and a dye image by development processing, after imagewise exposure, a silver halide photographic light-sensitive material containing a compound represented by formula (I)

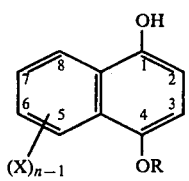

wherein R represents an alkyl group having from 6 to 22 carbon atoms, a substituted alkyl group having from 6 to 22 carbon atoms, an aryl group having from 6 to 22 carbon atoms, a substituted aryl group having from 6 to 22 carbon atoms, an alkenyl group having from 6 to 22 carbon atoms, a substituted alkenyl group having from 6 to 22 carbon atoms or an aralkyl group having from 7 to 22 carbon atoms; X represents an alkyl group having from 1 to 4 carbon atoms, an alkoxy group having from 1 to 6 carbon atoms or a halogen atom; and n represents an integer from 1 to 3.

DETAILED DESCRIPTION OF THE INVENTION

According to the process of the present invention, the preservation of the developer solution is markedly improved, since it is not necessary to add the alkoxynaphthols to a developer solution, and, also, the alkoxynaphthols represented by formula (I) do not dissolve out from the light-sensitive materials into the developer solution so as to accumulate therein. The photographic light-sensitive materials containing the alkoxynaphthols according to this invention do not suffer degradation due to oxidation by air, and have good durability. Also, since the alkoxynaphthol compound represented by formula (I) is used together with a high boiling point solvent (also referred to herein simply as the "high boiling solvent") having a high polarity according to the present invention, deposition of the compounds upon aging is prevented, and the stability of whole system is extraordinarily increased. Furthermore, by the combination of the solvent having a high polarity and the alkoxynaphthol compound represented by formula (I) according to the present invention, durability of the color images formed is outstandingly improved, which is valuable in practical use.

Photographic images formed by the process of the present invention may comprise both a silver image and a dye image, or only a dye image by removing at least a part of silver image by bleaching and fixing. This dye image is different from that in a conventional color photographic light-sensitive material, in that it is not formed by the reaction between a color coupler and an oxidation product of an aromatic primary amine developing agent. Also, it is different from the dye image formed by the autocoupling of a compound containing both a silver halide-developing moiety and a color coupler moiety in the same molecule (coupler-developer compound).

In more detail, representative conventional color forming process comprises (1) oxidizing a color developing agent by an exposed silver and then (2) reacting the resulting oxidized color developing agent with a color coupler to form a dye, as described, for example, in The Theory of Photographic Process, 4th Ed., pages 335 to 372 (Macmillan Co., 1977). On the other hand, according to the photographic image forming process of the present invention, the alkoxynaphthol compound represented by the formula (I) is oxidized by an exposed silver and the resulting oxidized alkoxynaphthol compound reacts with each other to form a dye.

The alkoxynaphthol compound represented by formula (I) is explained in greater detail below.

Examples of the substituents for the substituted alkyl group, the substituted aryl group, or the substituted alkenyl group in the formula (I) include a halogen atom (for example, a chlorine atom, a bromine atom, etc.), an amino group, a nitro group, a cyano group, an alkyl group, an alkoxy group, etc.

The alkyl group or the substituted alkyl group represented by R may be a straight chain or a branched chain and includes, for example, an n-hexyl group, an n-octyl group, an n-decyl group, an n-dodecyl group, an n-hexadecyl group, a 2,2-dimethylbutyl group, a 1,1-dimethylbutyl group, a diisobutylmethyl group, a 2-ethylhexyl group, a 1,7-dimethyloctyl group, a 2,6-dimethylheptyl group, a 4-propylhexyl group, a 1-methyl-1-ethylbutyl group, a 2-chloro-n-hexyl group, a 2,3-dibromo-n-dodecyl group, etc.

Examples of the aryl group or the substituted aryl group represented by R include a 4-chlorophenyl group, a 2,4-dichlorophenyl group, a 4-methoxyphenyl group, a 3-methoxyphenyl group, a 4-acetylphenyl group, a 4-acetamidophenyl group, a 4-octylphenyl group, a 4-hexylphenyl group, etc.

Examples of the alkenyl group represented by R include a 2-ethyl-2-butenyl group, a 3,5-dimethyl-2-pentenyl group, a 3,5-diethyl-2-heptenyl group, etc.

Examples of the aralkyl group represented by R include a benzyl group, a 1-phenylbutyl group, a 1-phenyl-1-methylethyl group, etc.

Of these functional groups, an alkyl group having from 8 to 16 carbon atoms, a substituted alkyl group having from 8 to 16 carbon atoms, an aryl group having from 6 to 16 carbon atoms, a substituted aryl group having from 6 to 22 carbon atoms, an alkenyl group having from 8 to 16 carbon atoms, a substituted alkenyl group having from 8 to 16 carbon atoms, and an aralkyl group having from 7 to 22 carbon atoms are preferred for R in formula (I).

Also, n is preferably up to 2 and X is preferably present at the 6 position or the 7-position with respect to the hydroxy group. More preferably n is 1.

Typical examples of specific compounds represented by formula (I) are set forth below. However, the present invention is not to be construed as being limited thereto.

I-1: 4-n-Hexyloxy-1-naphthol
I-2: 4-n-Octyloxy-1-naphthol
I-3: 4-n-Decyloxy-1-naphthol
I-4: 4-n-Dodecyloxy-1-naphthol
I-5: 4-n-Hexadecyloxy-1-naphthol
I-6: 4,7-Dihexyloxy-1-naphthol
I-7: 4-Hexyloxy-8-methoxy-1-naphthol
I-8: 4-Dodecyloxy-7-methoxy-1-naphthol
I-9: 4-Phenoxy-1-naphthol
I-10: 4-(β-Naphthyloxy)-1-naphthol
I-11: 4-Benzyloxy-1-naphthol
I-12: 4-Dodecyloxy-7-chloro-1-naphthol I-13: 4-Dodecyloxy-7-methyl-1-naphthol
I-14: 4-(4-Octylphenyloxy)-1-naphthol
I-15: 4-(4-Hexylphenyloxy)-1-naphthol
I-16: 4-Cyclohexyloxy-1-naphthol
I-17: 6,7-Dimethyl-4-hexyloxy-1-naphthol Of the naphthol derivatives used in the present invention, 4-alkoxy-1-naphthols are particularly preferred. Further, of the specific compounds described above, 4-n-octyloxy-1-naphthol, 4-n-decyloxy-1-naphthol, 4-n-dodecyloxy-1-naphthol, 4-n-hexadecyloxy-1-naphthol, 4-benzyloxy-1-naphthol, 4-phenyloxy-1-naphthol and 4-($\beta$-naphthyloxy)-1-naphthol are particularly preferred.

Syntheses of compounds of this type are described in the disclosures of A. Inoue, N. Kuroki and K. Konishi, *Bull. Univ. Osaka Prefect.*, A. 8, No. 1, pages 31 to 55 (1959), Japanese Patent Publication No. 21863/69, U.S. Pat. No. 2,572,822, *J.A.C.S.*, Vol. 61, page 2217 (1939).

Examples of synthesizing the naphthol derivatives represented by formula (I) used in the present invention are set forth below.

SYNTHESIS EXAMPLE 1

Synthesis of 4-n-Octyloxy-1-naphthol [Compound (I-2)]

216 g of naphthohydroquinone and 527 g of n-octyl alcohol were placed in a 2 l three-necked flask, and 114 ml of concentrated sulfuric acid was dropwisely added thereto for 30 minutes under nitrogen gas stream while stirring. Thereafter, the reaction mixture was heated at 50° C. for 1 hour and then cooled to room temperature. The reaction mixture was extracted with ethyl acetate. The ethyl acetate layer was washed with ammonia-water until the washing reached pH of 5 to 6. The ethyl acetate layer was further washed two times with an aqueous sodium chloride solution and, then, dried with anhydrous sodium sulfate. The dried ethyl acetate solution was concentrated under reduced pressure to precipitate crystals. The crystals were filtered off, and the filtrate was further concentrated under reduced pressure to distill off ethyl acetate and n-octyl alcohol to obtain oily substance. The oily substance was purified by column chromatography using a mixed solvent of n-hexane and ethyl acetate and, then, recrystallized from n-hexane to obtain 190 g of white crystals having a melting point of 73° to 74° C.

Elementary Analysis for $C_{18}H_{24}O_2$: Calculated C: 79.37%, H: 8.88%. Observed C: 79.55%, H: 8.63%.

SYNTHESIS EXAMPLE 2

Synthesis of 4-Cyclohexyloxy-1-naphthol [Compound (I-16)]

160 g of naphthohydroquinone and 416 g of cyclohexanol were placed in a 1 l three-necked flask, and 80 ml of concentrated sulfuric acid was dropwisely added thereto for 10 minutes under nitrogen gas stream while stirring. Thereafter, the reaction mixture was heated at 60° C. for 40 minutes and then cooled to room temperature. The reaction mixture was extracted with 500 ml of ethyl acetate. The ethyl acetate layer was washed with water until the washing reached neutral and, then, dried with MgSO₄ overnight. The dried ethyl acetate solution was concentrated under reduced pressure. The residue was distilled under reduced pressure to obtain 140 g of oily substance. The oily substance was dissolved in ethyl acetate and treated with about 20 g of active carbon followed by concentration under reduced pressure. The residue was recrystallized from benzene two times to obtain 60 g of white crystals having a melting point of 120° to 121° C.

Elementary Analysis for $C_{16}H_{18}O_2$: Calculated C: 79.31%, H: 7.49%. Observed C: 79.13%, H: 7.23%.

SYNTHESIS EXAMPLE 3

Synthesis of 4-n-Decyloxy-1-naphthol [Compound (I-3)]

112 g of naphthohydroquinone and 560 ml of n-decanol were placed in a 1 l three-necked flask and 56 ml of concentrated sulfuric acid was dropwisely added thereto for 30 minutes under nitrogen gas stream while stirring. Thereafter, the mixture was further stirred for 30 minutes and, then, heated at 50° C. for 1 hour and 30 minutes. After cooling, ethyl acetate-water was added to the reaction mixture and the precipitated crystals were filtered off. An aqueous sodium hydroxide solution was added to the filtrate so as to water layer reach pH of 5 to 6. Then, the ethyl acetate layer was washed with water and dried with MgSO₄ overnight. The dried ethyl acetate solution was evaporated under reduced pressure to remove ethyl acetate and n-decanol. The residue was dissolved in 1 l of ethyl acetate and treated with 26 g of active carbon followed by concentration under reduced pressure. The residue was recrystallized from a mixed solvent of ethyl acetate and n-hexane and, further, recrystallized from benzene to obtain 73 g of white crystals having a melting point of 89° to 90° C.

Elementary Analysis for $C_{22}H_{32}O_2$: Calculated C: 80.44%, H: 9.82%. Observed C: 80.15%, H: 9.67%.

SYNTHESIS EXAMPLE 4

Synthesis of 4-Hexyloxy-8-methoxy-1-naphthol [Compound (I-7)]

10 ml of hexyl alcohol and 50 ml of acetonitrile were placed in a 1 l three-necked flask, and 12.8 g of phosphorus oxychloride was dropwisely added thereto under cooling with ice while stirring. Thereafter, 9.5 g of $SnCl_2.2H_2O$ was added to the reaction mixture at room temperature. Then, 7.5 g of 8-methoxy-1,4-naphthoquinone was added to the reaction mixture at room temperature. The reaction mixture was refluxed for 2 hours on steam bath. The reaction mixture was poured into 1.2 l of diluted hydrochloric acid and extracted with 500 ml of ethyl acetate. The ethyl acetate solution was washed with water, dried with MgSO₄ overnight, and concentrated under reduced pressure to obtain 9 g of oily substance. The oily substance was purified by column chromatography using a mixed solvent of n-hexane and ethyl acetate and, then, recrystallized from benzene to obtain 6 g of white crystals having a melting point of 105° to 107° C.

Elementary Analysis for $C_{17}H_{22}O_3$: Calculated C: 74.42%, H: 8.08%. Observed C: 74.51%, H: 7.99%.

SYNTHESIS EXAMPLE 5

Synthesis of 6,7-Dimethyl-4-hexyloxy-1-naphthol [Compound (I-17)]

6,7-Dimethyl-1,4-naphthoquinone can be prepared by the method described in *J. Am. C. Soc.*, Vol. 61, page 2217 (1939). The same procedure as Synthesis Example 4 was carried out except for using 7.5 g of 6,7-dimethyl-1,4-naphthoquinone in place of 8-methoxy-1,4-naphthoquinone. Thereby, 4.3 g of desired 6,7-dimethyl-4-hexyloxy-1-naphthol was obtained as white crystals. melting point: 72°–73° C.

Elementary Analysis for C₁₈H₂₄O₂: Calculated: C: 79.37%, H: 8.88%. Observed C: 79.39%, H: 8.83%.

By using a high boiling organic solvent having a high polarity in the present invention, the fastness of the images obtained is improved, the dispersion of the alkoxynaphthol represented by formula (I) is rendered stable, and thus production aptitude of a photographic light-sensitive material is excellent, and in addition, the durability of dyes formed against light and heat is increased. According to the present invention, in addition to the above described effects, another great advantage is that the alkoxynaphthol represented by formula (I) can be easily and stably dispersed in a photographic light-sensitive material, and in addition, the maximum density of images obtained is increased.

The expression "high boiling point organic solvent having a high polarity" means an organic solvent having a dielectric constant at 25° C. (ε 25° C.) of from about 8 to 80, preferably from about 10 to 50, and a boiling point of from about 175° to about 350° C. Any organic solvent which satisfies the above described condition can be suitably used.

Examples of organic solvents which can be used are represented by formulae (II), (III), (IV), and (V) below.

The compound of formula (II) is represented by

(II)

wherein $R_1$, $R_2$, and $R_3$ each represents an alkyl group, an alkenyl group, an alkoxy group, an aryl group, or an aryloxy group, and each of these groups may be substituted. Examples of the substituents include a halogen atom, an alkoxy group, a cyano group, a carbonyl group, a carboxy group, etc.

The number of carbon atoms included in $R_1$, $R_2$ or $R_3$ is preferably from 1 to 20, and particularly preferably from 2 to 12.

Of the substituents for $R_1$ to $R_3$, an alkoxy group is generally used, and an alkoxy group substituted with a halogen atom is most preferred for the purpose of the present invention, since such a compound has a particularly high polarity.

The compound of formula (III) is represented by

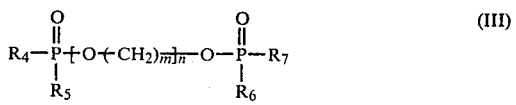
(III)

wherein $R_4$, $R_5$, $R_6$, and $R_7$ each represents an alkoxy group or aryloxy group, and each of these groups may be substituted. Examples of the substituents include a halogen atom, an alkoxy group, a cyano group, etc.

The number of carbon atoms included in $R_4$, $R_5$, $R_6$, or $R_7$ is preferably from 1 to 20, and particularly preferably from 2 to 12.

m is 1 to 8 and n is 0 to 8; preferably m is 1 to 4 and n is 0 to 4.

Those in which the alkoxy group or the aryloxy group represented by $R_4$ to $R_7$ is substituted with a halogen atom are most preferred for the purpose of the present invention because of their particularly high polarity.

The compound of formula (IV) is represented by

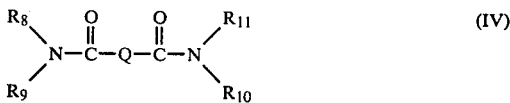
(IV)

wherein $R_8$, $R_9$, $R_{10}$, and $R_{11}$ each represents an alkoxy group or an aryloxy group and each of these groups may be substituted. Examples of the substituents include a halogen atom, an alkoxy group, a cyano group, etc.

The number of carbon atoms included in $R_8$, $R_9$, $R_{10}$, or $R_{11}$ is preferably from 1 to 20, and particularly preferably from 2 to 12.

Q represents a single chemical bond, a $-(CH_2)_n-$ group or a

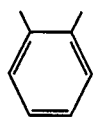

group wherein n is 1 to 8.

Those in which the alkoxy group or the aryloxy group represented by $R_8$ to $R_{11}$ is substituted with a halogen atom are most preferred for the purpose of the present invention because of their particularly high polarity.

The compound of formula (V) is represented by

(V)

wherein $R_{12}$, $R_{13}$, and $R_{14}$ each represents an alkyl group having from 1 to 20 carbon atoms (preferably from 1 to 12 carbon atoms) which may be substituted, an aryl group having from 6 to 20 carbon atoms (preferably from 6 to 16 carbon atoms) which may be substituted, or an alkenyl group. Examples of the substituents include a halogen atom, an alkoxy group, a cyano group, a carboxy group, etc.

Specific examples of the compounds represented by the above described formulae (II) to (V) are set forth below. However, the invention is not limited thereto.

(1)

(2)

(3)

(4)

(5)

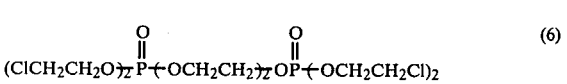
(6)

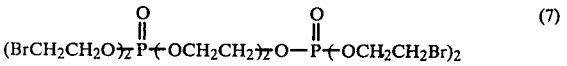
(7)

(8)

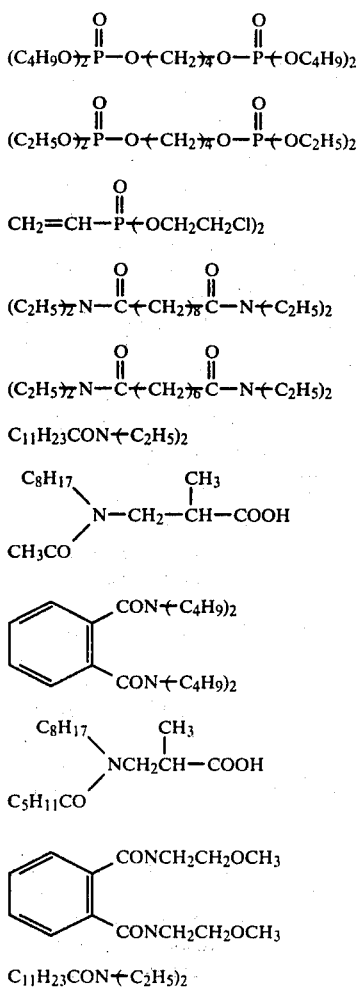

(9) (10) (11) (12) (13) (14) (15) (16) (17) (18) (19)

The naphthol derivative according to the present invention is added to the photographic light-sensitive material, for example, a hydrophilic colloid layer thereof. Preferably, the naphthol derivative according to the present invention is added to a silver halide emulsion layer.

In the case of incorporating the naphthol derivative described above into the photographic light-sensitive material, the naphthol derivative may be used in an amount of from 0.1 g/m² to 10 g/m², and preferably from 0.2 g/m² to 5 g/m². Also, the high boiling solvent may be used in an amount from 0.01 to 5 parts by weight, and preferably 0.2 to 3 parts by weight per part of the naphthol derivative used.

In order to introduce the naphthol derivative according to the present invention into a hydrophilic colloid constituting a photographic layer, it is preferred to use the methods described in U.S. Pat. Nos. 2,322,027 and 2,304,939, etc. That is, the naphthol derivative is dissolved in an organic solvent, emulsified and dispersed using a surface active agent, and the resulting emulsion dispersion is added to a photographic hydrophilic colloid. As the organic solvent suited for this purpose, a low boiling solvent having a boiling point of from about 30° C. to 150° C. may be used in combination in optional proportions in addition to the high boiling solvent having a high polarity described above. As the low boiling solvent, there can be used, e.g., an alcohol, an ether, a glycol, a ketone, an ester, and an amide.

According to the process of the present invention, a sufficiently high image density can be obtained in spite of using a low amount of coated silver in a silver halide photographic light-sensitive material. For the purpose of further accelerating development, a conventional developing agent can be used in combination.

Such developing agents include polyhydroxybenzenes (for example, hydroquinone, methylhydroquinone, t-butylhydroquinone, p-tolylhydroquinone, chlorohydroquinone, 2,4-dimethylhydroquinone, hydroquinonesulfonic acid and the salt thereof, bromohydroquinone, catechol, 4-methylcatechol, hydroxyhydroquinone, pyrogallol, etc.); aminophenols (for example, p-aminophenol, N-methyl-p-aminophenol (Metol), N,N-dimethyl-p-aminophenol, p-1-pyrrolidinophenol, 1-ethyl-6-hydroxy-1,2,3,4-tetrahydroquinoline, N,N-diethyl-p-aminophenol, etc.); 1-aryl-3-pyrazolidinones (for example, 1-phenyl-3-pyrrolidinone, 4,4-dimethyl-1-phenyl-3-pyrazolidinone, 4-hydroxymethyl-4-methyl-1-phenyl-3-pyrazolidinone, 1-p-tolyl-3-pyrazolidinone, etc.); and the like. These may be used alone or in combination of two or more thereof.

Of these developing agents, those which are preferable for the present invention include hydroquinone, t-butylhydroquinone, p-tolylhydroquinone, and bromohydroquinone, which are effective as the hydroquinone; N,N-diethyl-p-aminophenol, p-1-pyrrolidinophenol, and 1-ethyl-6-hydroxy-1,2,3,4-tetrahydroquinoline, which are effective as the aminophenol; and 1-aryl-3-pyrazolidinones wherein the aryl group is a phenyl group, which are effective as the 1-aryl-3-pyrazolidinones.

These developing agents may be used by incorporating into a photographic light-sensitive material as well as by adding to a developer solution.

In the process of the present invention, 3-pyrazolidones or hydroquinones may be used alone or in combination as auxiliary developing agents by adding to a developer solution or by incorporating into a photographic light-sensitive material.

The 3-pyrazolidones which can be preferably used in the present invention are represented by formula (VI)

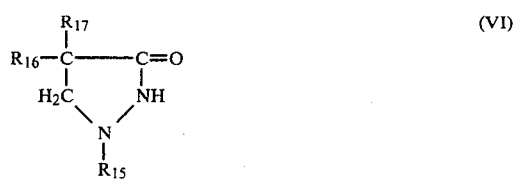

(VI)

wherein $R_{15}$ represents an aryl group, and $R_{16}$ and $R_{17}$ each represents a hydrogen atom, an alkyl group, or a hydroxyalkyl group.

The aryl group represented by $R_{15}$ is preferably a phenyl group. Preferably, this aryl group is not substituted.

The alkyl group represented by $R_{16}$ or $R_{17}$ preferably contains from 1 to 4 carbon atoms and is illustrated by, for example, a methyl group, an ethyl group, an n-propyl group, an i-propyl group, an n-butyl group, a tert-butyl group, and so forth.

Examples of the hydroquinones which can be incorporated into the photographic light-sensitive material used in the process of the present invention include hydroquinone, a mono- or dialkylhydroquinone (the number of carbon atoms included in the alkyl group being 1 to 4) or an arylhydroquinone.

The silver image formed by the process of the present invention is substantially black, but it includes images tinged with other colors, such as brown or blue. The dye image formed by the process of the present invention may be of any color as long as it has an absorption in the visible region of the spectrum. This dye image lies on the silver image to increase the total image density and, therefore, enables one to reduce the amount of coated silver necessary to obtain a desired image density.

The processing steps used in the present invention comprise a developing step and a fixing step and, if desired, a water-washing step and a stopping step may be provided. A drying step may also be provided at the end of the processing steps.

The processing temperature is usually from 10° C. to 70° C., and preferably from 20° C. to 60° C.

The pH of the alkaline processing solution used in the present invention is generally from 7 to 14, are preferably from 10 to 13.

The alkaline processing solution used in the present invention may also contain other known developer component compounds besides the above described developing agents and 3-pyrazolidones. For example, as an alkali agent, a buffer agent, etc., sodium hydroxide, potassium hydroxide, sodium carbonate, potassium carbonate, sodium or potassium tertiary phosphate, potassium metaborate, borax, etc., may be used alone or in combination. Also, in order to impart buffering action or raise the ionic strength of the developer, etc., there may further be used various salts such as disodium or dipotassium hydrogen phosphate, potassium or sodium dihydrogen phosphate, sodium or potassium bicarbonate, boric acid, alkali metal nitrates, alkali metal sulfates, etc.

An antifogging agent may optionally be incorporated into the alkaline processing solution used in the present invention. As such an antifogging agent, alkali metal halides (e.g., potassium bromide, sodium bromide, potassium iodide, etc.) and organic antifogging agents can be used. Examples of organic antifogging agent include nitrogen-containing hetero ring compounds (e.g., benzotriazole, 6-nitrobenzimidazole, 5-nitroisoindazole, 5-methylbenzotriazole, 5-nitrobenzotriazole, 5-chlorobenzotriazole, etc.), mercapto-substituted hetero ring compounds (e.g., 1-phenyl-5-mercaptotetrazole, 2-mercaptobenzimidazole, 2-mercaptobenzothiazole, etc.), and mercapto-substituted aromatic compounds (e.g., thiosalicylic acid). Particularly preferred antifogging agents are nitrogen-containing hetero ring compounds, especially nitrogen-containing hetero ring compounds not substituted by a mercapto group. The antifogging agents are generally used in an amount of from 1 mg to 5 g, and preferably from about 5 mg to 1 g, per 1 liter of the alkaline processing solution.

Further, hydroxylamine sulfate or hydrochloride, sodium sulfite, potassium sulfite, potassium bisulfite, or sodium bisulfite can be added to the alkaline processing solution used in the present invention.

Optionally development accelerators may be added to the alkaline processing solution, if necessary. Specific examples of the development accelerators are described, for example, in Research Disclosure, Vol. 176, Item 17643, pages 29 to 30 (Dec. 1978), L. F. A. Mason, Photographic Processing Chemistry, 2nd Ed., pages 41 to 44 (Focal Press, London, 1975), etc.

The naphthol derivative according to the present invention can be introduced into a hydrophilic colloid consituting a photographic light-sensitive material in any of the steps for producing photographic light-sensitive materials, with the steps prior to coating, and in particular the step of preparing the photographic coating solution, being desirable.

Ordinary photographing materials generally contain from 3 to 10 g/m$^2$ silver salts (calculated as silver), and printing materials generally contain about from 1 to 4 g/m$^2$ silver. On the other hand, the photographic material according to the present invention contains coated silver in an amount of not more than 5 g/m$^2$, and in general the amount of silver can be reduced 20% in comparison with an analogous conventional type photographic material put to the same use.

A silver halide emulsion is usually prepared by mixing a solution of water-soluble silver salt (e.g., silver nitrate, etc.) with a solution of a water-soluble halide (e.g., potassium bromide, etc.) in the presence of a solution of a water-soluble polymer such as gelatin. As the silver halide, mixed silver halides such as silver chlorobromide, silver iodobromide, silver chloroiodobromide, etc., as well as silver chloride and silver bromide can be used.

Such silver halide emulsions are described in Research Disclosure, Vol. 176, Item 17643, pages 22 to 23 (Dec. 1978); T. H. James, Theory of Photographic Process, 4th Ed. (published by Macmillan Co., 1977); P. Glafkides, Chimie Photographique, 4th Ed. (published by Paul Montel, 1976), and the like, and can be prepared according to various processes commonly accepted, such as an ammoniacal process, a neutral process, an acidic process, etc.

The above described silver halide emulsion can be chemically sensitized in the conventional manner. As the chemical sensitizing agents, there are described in the references and books cited with respect to the preparation of silver halide emulsion described above, for example, The Theory of Photographic Process, 4th Ed. (published by Macmillan Co., 1977), p. 149.

In some cases, it is preferable to further add various additives in order to obtain a particular desired development property, image property, film property, etc. As such additives, salt form iodides, organic compounds having a mercapto free group such as phenylmercaptotetrazole, etc., and alkali metal iodide salts may be incorporated. However, it is desirable to avoid using them in excessively large amounts since excessively large amounts thereof reduce sensitivity.

Conventional antifogging agents added to a light-sensitive silver halide emulsion layer and a nonlight-sensitive auxiliary layer of a photographic light-sensitive material may be used in combination with the compound of the present invention. As other additives, a hardener, a plasticizer, a lubricant, a surface brightening agent and others known in the photographic field may be incorporated in the photographic light-sensitive material.

As the hydrophilic colloid, there are illustrated, for example, gelatin, colloidal albumin, casein, cellulose derivatives (e.g., carboxymethyl cellulose, hydroxyethyl cellulose, etc.), sugar derivatives (e.g., agar-agar, sodium alginate, starch derivative, etc.), and synthetic hydrophilic colloids (e.g., polyvinyl alcohol, poly-N-vinyl pyrrolidone, polyacrylic acid copolymer, polyacrylamide, the derivatives (including partially hydrolyzed products) thereof, etc.). If necessary, a compatible mixture of two or more of these colloids may be used. Of these, the most generally used is gelatin. Gelatin can be replaced partially or wholly by a synthetic polymer and, in addition, so-called gelatin deriatives may be used.

The photographic emulsions may, if desired, be subjected to spectral sensitization or supersensitization using cyanine dyes such as cyanine, merocyanine, carbocyanine, etc., alone or in combination, or in further combination with styryl dyes, etc. These color-sensitizing techniques are described, for example, in the disclosure in *Research Diclosure,* Vol. 176, Item 17643, page 23 (Dec. 1978). While various color-sensitizing techniques are described in the above reference, suitable techniques can be selected based on the end-use of the light-sensitive materials such as the wavelength region to be sensitized, the sensitivity, and the like.

As the photographic support, a polymer film, a metal sheet, a thin glass, paper, ceramics, etc., commonly used for photographic light-sensitive materials can be used herein. Specific examples are desribed, for example, in *Research Disclosure,* Vol. 176, Item 17643, page 28 (Dec. 1978).

As the suitable supports, transparent or opaque supports can be selected depending upon the intended end-use of the photographic light-sensitive materials. Also, with transparent supports, not only transparent, colorless ones, but transparent supports colored by adding dyes or pigments can be used as well. This has heretofore been conducted with X-ray film and is disclosed, for example, in *Journal of the Society of Motion Picture and Television Engineers,* 67, page 296 (1958), etc.

The photographic element layer used in the practice of the present invention may be coated according to various coating methods including dip-coating, airknife coating, curtain coating, and extrusion coating using a hopper as described in U.S. Pat. No. 2,681,294.

Furthermore, the features of other image intensifying methods, such as those as cited below, can also be utilized in combination with the method of the present invention.

Descriptions on various photographic processes utilizing decomposition of a peroxide on the surface of a noble metal are found in West German Patent Application (OLS) Nos. 1,813,920, 1,950,102, 1,955,901, 1,961,029, 2,044,833, 2,044,993, 2,056,360, 2,056,359 and 2,120,091, etc. On the other hand, color-intensifying processes utilizing cobalt complex salts on the surface of noble metal are described, for example, in Japanese Patent Application (OPI) Nos. 9728/73, 9729/73, 48130/73, 84229/74, 84239/74, 84240/74, 97614/74, 102340/74 and 102341/74, etc. Also, a color-intensifying process using a halide such as a chlorite is described in Japanese Patent Application (OPI) No. 53826/76 and Japanese Patent Application (OPI) No. 99022/76.

The present invention is now described in more detail by reference to the following examples. However, the invention is not limited thereto.

EXAMPLE 1

Each of the compounds according to the present invention as set forth in Table 1 below and comparative compounds, i.e., 4-methoxy-1-naphthol and 4-butoxy-1-naphthol, was dissolved in tricresyl phosphate and the solution was emulsified and dispersed in an aqueous gelatin solution to prepare an emulsion (in which a ratio of oil to coupler was 2/1). This emulsion was mixed with a silver iodobromide photographic emulsion (diode: 1.5 mol %) having a mean particle size of 1.4 $\mu$m and the mixture was coated on a polyethylene terephthalate film in an amount of 40 mg/dm$^2$ of silver. The amount of the 4-alkoxy-1-naphthol was set up to 0.5 mol per mol of silver. On the light-sensitive layer, a gelatin protective layer was coated to prepare photographic light-sensitive materials (a) to (h). Furthermore, in the same manner as described above, except that the naphthol derivative was omitted, a photographic light-sensitive material (i) was prepared for comparison.

Each of the photographic light-sensitive materials (a) to (i) thus prepared was exposed through a light wedge and subjected to processing with the following two kinds of developer solutions using a roller-conveying type processor.

| Step | Processing Temperature | Processing Time |
| --- | --- | --- |
| Development | 35° C. | 25 sec |
| Fixing | 34° C. | 25 sec |
| Washing | 33° C. | 25 sec |
| Drying | 35° C. | 15 sec |

The compositions of the developer solution and the fixing solution used are as follows.

Developer Solution A

| | |
| --- | --- |
| Sodium Sulfite | 40 g |
| Sodium Hydroquinonesulfonate | 15 g |
| 4-Hydroxymethyl-4-methyl-1-phenyl-3-pyrazolidone | 2 g |
| Trisodium Phosphate (12 hydrate) | 50 g |
| Sodium Bromide | 10 g |
| 5-Methylbenzotriazole | 0.05 g |
| Sodium Hydroxide | 6.4 g |
| Water to make | 1 l |

The pH of the developer solution was about 12.5 at 25° C.

Developer Solution B

A developer solution having the same composition as Developer Solution A, except that 50 cc per liter of a 10% methanol solution of 4-methoxy-1-naphthol was added. The pH of the developer solution was about 12.5 at 25° C.

Fixing Solution

| | |
| --- | --- |
| Ammonium Thiosulfate | 175 g |
| Sodium Sulfite (anhydrous) | 15 g |
| Glacial Acetic Acid | 12 ml |
| Sodium Metaborate | 15 g |
| Potassium Alum | 20 g |
| Water to make | 1 l |

The pH of the fixing solution as about 5.0 at 25° C.

The maximum density and fog value obtained with respect to a combination of a photographic light-sensitive material and a developer solution are listed in Table 1 below. It is apparent by comparing Tests 1 to 8 with Test 9 that the maximum densities obtained from the photographic light-sensitive materials containing the naphthol derivative according to the present invention are remarkably high in comparison with that obtained from the photographic light-sensitive material (i) which does not contain the naphthol derivative. That is, the optical densities were increased in proportion to the amount of dye formed, and a saving of silver in a corresponding amount can be obtained. Further, it is understood by comparing Tests 3 to 8 with Tests 1 and 2, the photographic light-sensitive materials containing the naphthol derivative according to the present invention provide higher maximum densities comparing with the light-sensitive material containing 4-methoxy-1-naphthol or 4-butoxy-1-naphthol, and thus the present invention provides a more effective means for saving silver than has existed heretofore.

Also, in Table 1, the results of testing in which the photographic properties and the coloration of developer solution were compared using developer solutions stored under the conditions described below, in order to determine preservability of the developer solutions.

(1) Developer solution was allowed to stand in a beaker for 2 days after preparation (natural durability test).

(2) Developer solution with which 1.72 m²/liter of each of the photograhic light-sensitive materials (a) to (i) was processed (running durability test).

bility and running aptitude of the developer solution are extremely improved.

EXAMPLE 2

The photographic light-sensitive materials (a) and (e) described in Example 1 were exposed to white light and processed in the same manner as described in Example 1 using Developer Solution A. Using the photographic material thus processed the following analysis was conducted.

The amount of developed silver in the photographic material was measured using $\gamma$-ray fluorescent analysis. The results obtained are shown in Table 2 below. On the other hand, the amount of dyes formed in the photographic material was determined in the following manner. A predetermined size of the photographic material was immersed in an aqueous solution containing an enzyme at 35° C. to decompose gelatin, the aqueous phase was extracted with ethyl acetate and the spectral absorption of the organic solvent phase was measured to determine the amount of dyes formed. The results

TABLE 1

| Test No. | Light-Sensitive Material | Alkoxynaphthol Compound | Developer Solution |
|---|---|---|---|
| 1 | (a) | 4-Methoxy-1-naphthol | A |
| 2 | (b) | 4-Butoxy-1-naphthol | A |
| 3 | (c) | 4-n-Hexyloxy-1-naphthol (I-1) | A |
| 4 | (d) | 4-n-Octyloxy-1-naphthol (I-2) | A |
| 5 | (e) | 4-n-Dodecyloxy-1-naphthol (I-3) | A |
| 6 | (f) | 4-Phenyloxy-1-naphthol (I-9) | A |
| 7 | (g) | 4-Benzyloxy-1-naphthol (I-11) | A |
| 8 | (h) | 4-(4-Octylphenyloxy)-1-naphthol (I-14) | A |
| 9 | (i) | — | A |
| 10 | (i) | — | B |

| | Just after Preparation | | | Natural Durability | | | Running Durability | | | |
|---|---|---|---|---|---|---|---|---|---|---|
| Test No. | $D_{max}$ | Fog | Color of Processing Solution | $D_{max}$ | Fog | Color of Processing Solution | $D_{max}$ | Fog | Color of Processing Solution | Color of Image |
| 1 | 3.08 | 0.23 | colorless | 3.00 | 0.25 | colorless | 3.25 | 0.56 | deep blue (precipitation) | blue black |
| 2 | 3.14 | 0.23 | " | 3.12 | 0.26 | " | 3.33 | 0.61 | blue | blue |
| 3 | 3.03 | 0.21 | " | 3.22 | 0.24 | " | 3.30 | 0.26 | colorless | blue |
| 4 | 3.28 | 0.23 | " | 3.20 | 0.23 | " | 3.21 | 0.23 | " | blue black |
| 5 | 3.32 | 0.22 | " | 3.30 | 0.24 | " | 3.25 | 0.23 | " | blue black |
| 6 | 2.99 | 0.21 | " | 3.02 | 0.22 | " | 3.10 | 0.22 | " | blue |
| 7 | 3.22 | 0.24 | " | 3.22 | 0.24 | " | 3.30 | 0.26 | " | blue |
| 8 | 3.30 | 0.24 | " | 3.02 | 0.23 | " | 3.28 | 0.24 | " | blue black |
| 9 | 1.63 | 0.21 | " | 1.63 | 0.22 | " | 1.63 | 0.23 | " | yellow black |
| 10 | 2.86 | 0.53 | " | 2.99 | 0.83 | blue | 3.04 | 0.98 | blue | blue black |

From the results shown in Table 1 above, it is apparent that when the alkoxynaphthol derivative is added to a developer solution, the compound is readily oxidized by air and a high level of fog is formed, as shown in Test No. 10. On the other hand, the preservability of the developer is improved by incorporating the alkoxynaphthol derivative into the light-sensitive material as shown in Test Nos. 1 to 8. However, when 4-methoxy-1-naphthol or 4-butoxy-1-naphthol is used, the naphthol derivative dissolves out into the processing solution during the processing, and accumulates in the processing solution by the repetition of development, resulting in the contamination of the processing solution and the formation of severe fog as shown in Test Nos. 1 and 2. That is, it ends in the same disadvantageous results as using the naphthol derivative in the developer solution. On the contrary, when the compounds according to the present invention are used, stable properties are obtained even when the processing was repeated, as is shown in Test Nos. 3 to 8. This means that the preservaobtained are shown in Table 2.

TABLE 2

| | | Silver Developed | | Dye Formed | |
|---|---|---|---|---|---|
| Test No. | Light-Sensitive Material | Amount of Silver Developed (mg/dm²) | Amount of Silver Developed/ Amount of Silver Coated (%) | Amount of Dye Formed (mmol/m²) | Amount of Dye formed/ Amount of Compound Coated (%) |
| 11 | (e) | 38.2 | 95 | 5.56 | 63.0 |
| 12 | (a) | 37.3 | 92 | 3.85 | 42.2 |

As is apparent from the results shown in Table 2, when the alkoxynaphthol derivative according to the present invention is used (in Test No. 11), the amount of dye formed per the amount of coated silver is highly increased in comparison with the case in which the comparison compound was used (in Test No. 12). This is believed to be based on the fact that the dyes formed are effectively employed for forming the images because the alkoxynaphthol derivative does not dissolve out into the processing solution.

While the invention has been described in detail and with reference to specific embodiments thereof, it will be apparent to one skilled in the art that various changes and modifications can be made therein without departing from the spirit and scope thereof.

What is claimed is:

1. A process for forming a photographic image comprising imagewise exposing a silver halide photographic light-sensitive material to light and development processing the exposed silver halide photographic light-sensitive material with an alkaline processing solution having a pH of 10 to 13 and in the presence of an auxiliary developing agent, wherein the silver halide photographic light-sensitive material contains, as a developing agent, an alkoxynaphthol compound, which is represented by formula (I)

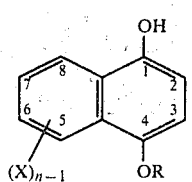 (I)

wherein R represents an alkyl group having from 6 to 22 carbon atoms, a substituted alkyl group having from 6 to 22 carbon atoms, an aryl group having from 6 to 22 carbon atoms, a substituted aryl group having from 6 to 22 carbon atoms, an alkenyl group having from 6 to 22 carbon atoms, a substituted alkenyl group having from 6 to 22 carbon atoms or an aralkyl group having from 7 to 22 carbon atoms; X represents an alkyl group having from 1 to 4 carbon atoms, an alkoxy group having from 1 to 6 carbon atoms, or a halogen atom; and n represents an integer from 1 to 3, said alkoxynaphthol compound being oxidized by the silver in said exposed silver halide photographic light sensitive material during development processing with the resulting oxidized alkoxynaphthol compound reacting together to form a dye.

2. A process for forming a photographic image as in claim 1, wherein R represents an alkyl group having from 8 to 16 carbon atoms, a substituted alkyl group having from 8 to 16 carbon atoms, an aryl group having from 6 to 16 carbon atoms, a substituted aryl group having from 6 to 22 carbon atoms, an alkenyl group having from 8 to 16 carbon atoms, a substituted alkenyl group having from 8 to 16 carbon atoms, or an aralkyl group having from 7 to 22 carbon atoms.

3. A process for forming a photographic image as in claim 1, wherein n is 1 or 2 and X is present at the 6-position or the 7-position with respect to the hydroxy group.

4. A process for forming a photographic image as in claim 1, wherein n is 1.

5. A process for forming a photographic image as in claim 1, wherein the compound is a 4-alkoxy-1-naphthol.

6. A process for forming a photographic image as in claim 1, wherein the compound is present in a hydrophilic colloid layer of the silver halide photographic light-sensitive material.

7. A process for forming a photographic image as in claim 1, wherein the compound is present in a silver halide emulsion layer of the silver halide photographic light-sensitive material.

8. A process for forming a photographic image as in claim 6, wherein the compound is present together with an organic solving having a boiling point of from about 175° C. to about 350° C. and having a high polarity as measured by a dielectric constant at 25° C. of from about 8 to 80.

9. A process for forming a photographic image as in claim 8, wherein the high boiling point organic solvent is an organic solvent having a dielectric constant at 25° C. of from about 10 to about 50.

10. A process for forming a photographic image as in claim 8, wherein the organic solvent is represented by formula (II)

 (II)

wherein $R_1$, $R_2$, and $R_3$ each represents an alkyl group, an alkenyl group, an alkoxy group, an aryl group, or an aryloxy group.

11. A process for forming a photographic image as in claim 8, wherein the organic solvent is represented by formula (III)

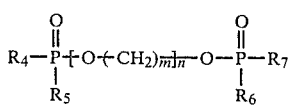 (III)

wherein $R_4$, $R_5$, $R_6$, and $R_7$ each represents an alkoxy group or an aryloxy group; m is 1 to 8; and n is 0 to 8.

12. A process for forming a photographic image as in claim 8, wherein the organic solvent is represented by the following formula (IV)

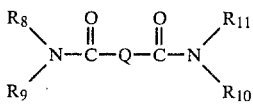 (IV)

wherein $R_8$, $R_9$, $R_{10}$ and $R_{11}$ each represents an alkoxy group or an aryloxy group; Q represents a single chemical bond, a $-(CH_2)_n-$ group or a

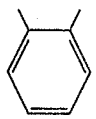

group wherein n is 1 to 8.

13. A process for forming a photographic image as in claim 8, wherein the organic solvent is represented by formula (V)

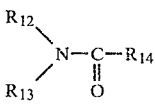 (V)

wherein $R_{12}$, $R_{13}$ and $R_{14}$ each represents an alkyl group, an aryl group, or an alkenyl group.

14. A process for forming a photographic image as in claim 1, 2, 3, 4, 5, 6, 7, 8, 9, 10, 11, 12, or 13, wherein said alkoxynaphthol compound is present in an amount of from 0.1 g/m² to 10 g/m².

15. A process for forming a photographic image as in claim 8, wherein the organic solvent is present in an amount of 0.01 to 5 parts by weight per part of the alkoxynaphthol compound.

16. A process for forming a photographic image as in claim 1, wherein the auxiliary developing agent is a 3-pyrazolidone.

17. A process for forming a photographic image as in claim 16, wherein the 3-pyrazolidone is represented by formula (VI)

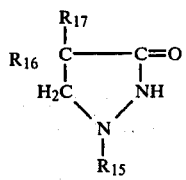 (VI)

wherein $R_{15}$ represents an aryl group, and $R_{16}$ and $R_{17}$ each represents a hydrogen atom, an alkyl group, or a hydroxyalkyl group.

18. A process for forming a photographic image as in claim 17, wherein $R_{15}$ represents a phenyl group.

19. A process for forming a photographic image as in claim 1, wherein the auxiliary developing agent is present in the alkaline processing solution.

20. A process for forming a photographic image as in claim 1, wherein the alkaline processing solution contains a developing agent.

21. A process for forming a photograph image as in claim 1, wherein the process comprises said development processing and additionally a fixing step.

22. A process for forming a photographic image as in claim 1, wherein the photographic light-sensitive material contains silver halide in an amount of coated silver of not more than 5 g/m².

23. A process for forming a photographic image as in claim 14, wherein said alkoxynaphthol compound is present in an amount of from 0.2 g/m² to 6 g/m².

24. A process for forming a photographic image as in claim 15, wherein the organic solvent is present in an amount of from 0.2 to 3 parts by weight per part of the alkoxynaphthol compound.

* * * * *